(12) United States Patent
Ulfendahl

(10) Patent No.: US 6,280,954 B1
(45) Date of Patent: Aug. 28, 2001

(54) ARRAYED PRIMER EXTENSION TECHNIQUE FOR NUCLEIC ACID ANALYSIS

(75) Inventor: Per Johan Ulfendahl, Uppsala (SE)

(73) Assignee: Amersham Pharmacia Biotech AB, Uppsala (SE)

(*) Notice: Subject to any disclaimer, the term of this patent is extended or adjusted under 35 U.S.C. 154(b) by 0 days.

(21) Appl. No.: 09/601,258

(22) PCT Filed: Feb. 2, 1999

(86) PCT No.: PCT/EP99/00918

§ 371 Date: Sep. 19, 2000

§ 102(e) Date: Sep. 19, 2000

(87) PCT Pub. No.: WO99/39001

PCT Pub. Date: Aug. 5, 1999

(30) Foreign Application Priority Data

Feb. 2, 1998 (EP) .................................................. 98300741

(51) Int. Cl.[7] .............................. C12Q 1/68; C12P 19/34
(52) U.S. Cl. ............................. 435/6; 435/91.1; 435/91.2
(58) Field of Search ............................. 435/6, 91.1, 91.2, 435/810

(56) References Cited

U.S. PATENT DOCUMENTS

| | | | |
|---|---|---|---|
| 5,503,980 | * | 4/1996 | Cantor ....................................... 435/6 |
| 5,981,176 | * | 11/1999 | Wallace ..................................... 435/6 |
| 6,004,744 | * | 12/1999 | Goelet et al. ............................. 435/5 |
| 6,103,463 | * | 8/2000 | Chetverin et al. ........................ 435/6 |
| 6,156,502 | * | 12/2000 | Beattie ...................................... 435/6 |

FOREIGN PATENT DOCUMENTS

93/17126 * 9/1993 (WO) .
97/22720 * 6/1997 (WO) .

* cited by examiner

Primary Examiner—Kenneth R. Horlick
(74) Attorney, Agent, or Firm—Marshall, O'Toole, Gerstein, Murray & Borun

(57) ABSTRACT

A nucleic acid analysis method is provided which includes the steps of using a primer to amplify the nucleic acid; providing an array of probes, each probe comprising a sequence identical to the primer and an adjacent sequence; applying fragments of the amplifier nucleic acid under hybridisation conditions to the array, effecting enzymatic chain extension of any probe where the adjacent sequence matches that of a hybridised fragment of the amplified nucleic acid; and observing the location of probes of the array while chain extension has taken place.

16 Claims, 10 Drawing Sheets

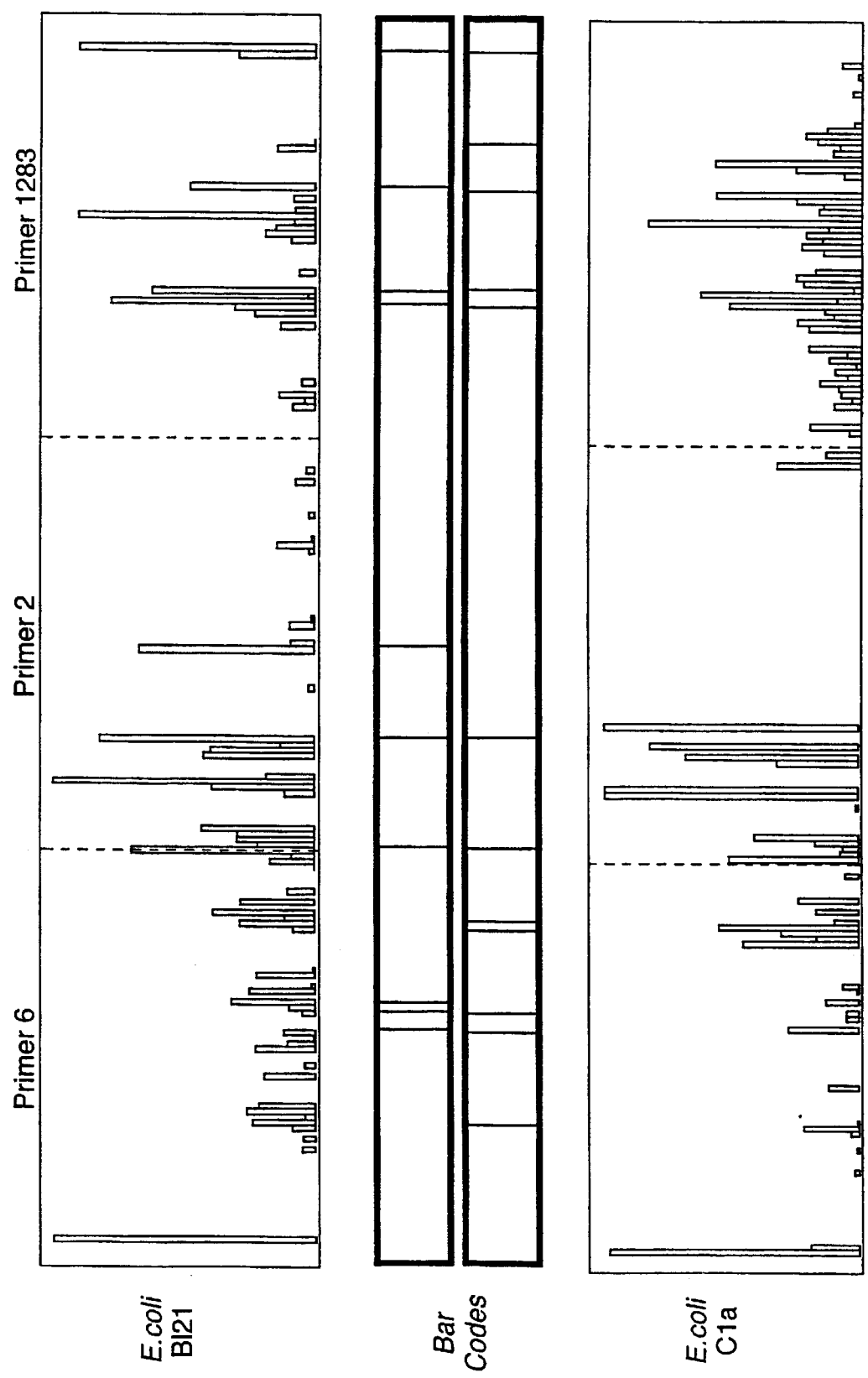

Serotype 1

Serotype 2

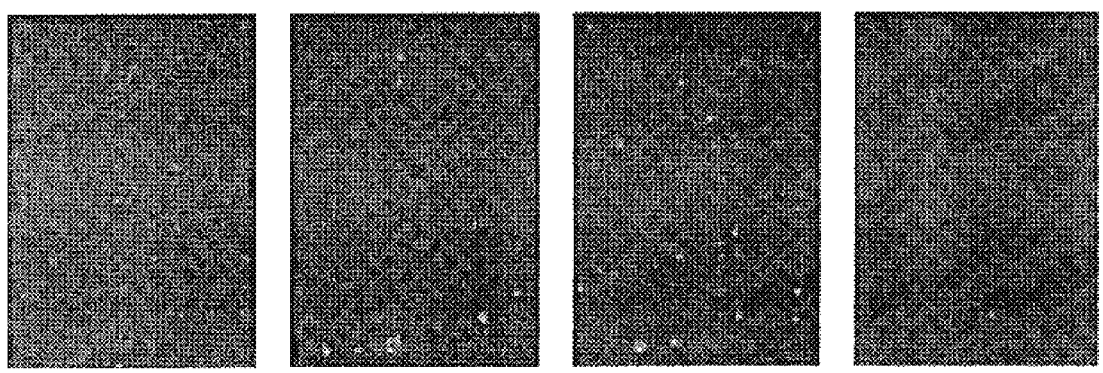
Fig.4(iii).
Serotype 4a

Serotype 4b

ATCC 15313

ATCC 35152

US 6,280,954 B1

ARRAYED PRIMER EXTENSION TECHNIQUE FOR NUCLEIC ACID ANALYSIS

BACKGROUND

This invention concerns the characterisation, classification, identification and typing of different DNA containing organisms such as plants, animals, bacteria and their viruses.

The science of detecting genomic polymorphisms is quickly evolving, and several techniques have been developed to compare the genomes of different organisms. These techniques utilise the whole genome or segments thereof for comparison purposes and are often referred to as DNA fingerprinting techniques. The main application fields for these techniques are gene mapping, detection of bacterial strain diversity, population analysis, epidemiology, gene expression and the demonstration of phylogenetic and taxonomic relationships.

In the application areas of bacterial identification and typing, pulsed-field gel electrophoresis, random amplified polymorphic DNA (RAPD) and DNA sequencing of different genes are frequently discussed as methods of the future, compared to traditional methods based on biochemical and growth properties. The drawback with all these and other suggested DNA fingerprinting methods is the use of electrophoresis. This is because electrophoresis is a laborious separation technology and the time from start to finish is long, ranging from 30 minutes up to more than 20 hours for pulsed-field gel electrophoresis, followed by both detection of the DNA and analysis of the results.

Since ribosomes are present in all living organisms, and the ribosomes contain three kinds of rRNA (in bacteria 5 S, 16 S, and 23 S), DNA sequencing of the corresponding genes is frequently used for characterisation, identification and taxonomy relations of bacteria, fungi and other organisms. The most widely used of the ribosomal genes is 16 S rDNA. The DNA sequences of these genes contain well-defined segments of different evolutionary variability regions, which in the 16 S rRNA molecule are referred to as universal, semi-conserved and variable regions. Oligbnucleotide primers complementary to universal regions can be used for amplification of ribosomal RNA from any organism or bacteria, the generated ribosomal fragment being then sequenced. In a computer search against a database with all known ribosomal sequences the species can be assigned.

Random amplified polymorphic DNA (RAPD) is a process for detecting polymorphisms on the basis of nucleotide differences and is covered by U.S. Pat. No. 5,126,239 of Livak et al, 1992. RAPD analysis is one of the most sensitive, reproducible and efficient methods currently available in the research field for distinguishing different strains and isolates of a species. RAPD analysis is a technique that uses a single short oligonucleotide primer of arbitrary sequence in a low stringency amplification reaction (Welsh J and McClelland M, 1990, Nucleic Acids Research, 18 (24), 7213–7218; Williams J G et al (1990) Nucleic Acids Research, 18, 6531–6535). The generated DNA fragments are subsequently analysed by gel electrophoresis. Analysis can either be done automatically on line with an automated DNA sequencer or on any electrophoresis gel and stained with ethidium bromide or silver.

In arrayed primer extension techniques (APEX), primers which have hybridised with a template, having a free 3'-end and having a free hydroxyl group, can be extended with free dNTPs and a DNA polymerase. If ddNTPs or other chain terminators are added to the mixture the elongation will terminate at that point. A similar method to this was developed for mutation detection (WO 91/13075). The authors used a PCR template bound to wells of a microtitre plate, and the primers were added for extension after binding to the template.

Further development of this method was carried out where consecutive primers overlapping each other by one base were bound to a support in the form of an array (also called a DNA chip). These were bound to the surface by the 5'-end, so that the 3'-end was free for elongation after addition of template, ddNTP and a polymerase. The chain terminating molecules were labelled, with any type of chromophore, fluorophore, isotope or antibody reactive reagent. This technique is described in WO 95/00669.

BRIEF SUMMARY OF THE INVENTION

The present invention combines features of random amplified polymorphic DNA (RAPD) and of arrayed primer extension (APEX), techniques, so as to avoid the difficulty and delay of gel electrophoresis.

In one aspect, the invention provides a nucleic acid analysis method which comprises:

a) using a primer to amplify the nucleic acid, b) providing an array of probes in which each probe comprises a primer sequence that is identical to (or complementary to) the sequence of the primer, and an adjacent sequence which is different in each probe of the array, c) applying the amplified nucleic acid from a) under hybridisation conditions to the array of b), d) effecting enzymatic chain extension of any probe where the adjacent sequence matches that of the hybridised amplified nucleic acid, and e) observing the location of probes of the array where chain extension has taken place in d).

BRIEF DESCRIPTION OF THE SEVERAL VIEWS OF THE DRAWINGS

FIG. 3 depicts bacterial grouping data obtained by practice of the method of the invention;

DETAILED DESCRIPTION OF THE INVENTION

Figure 1:
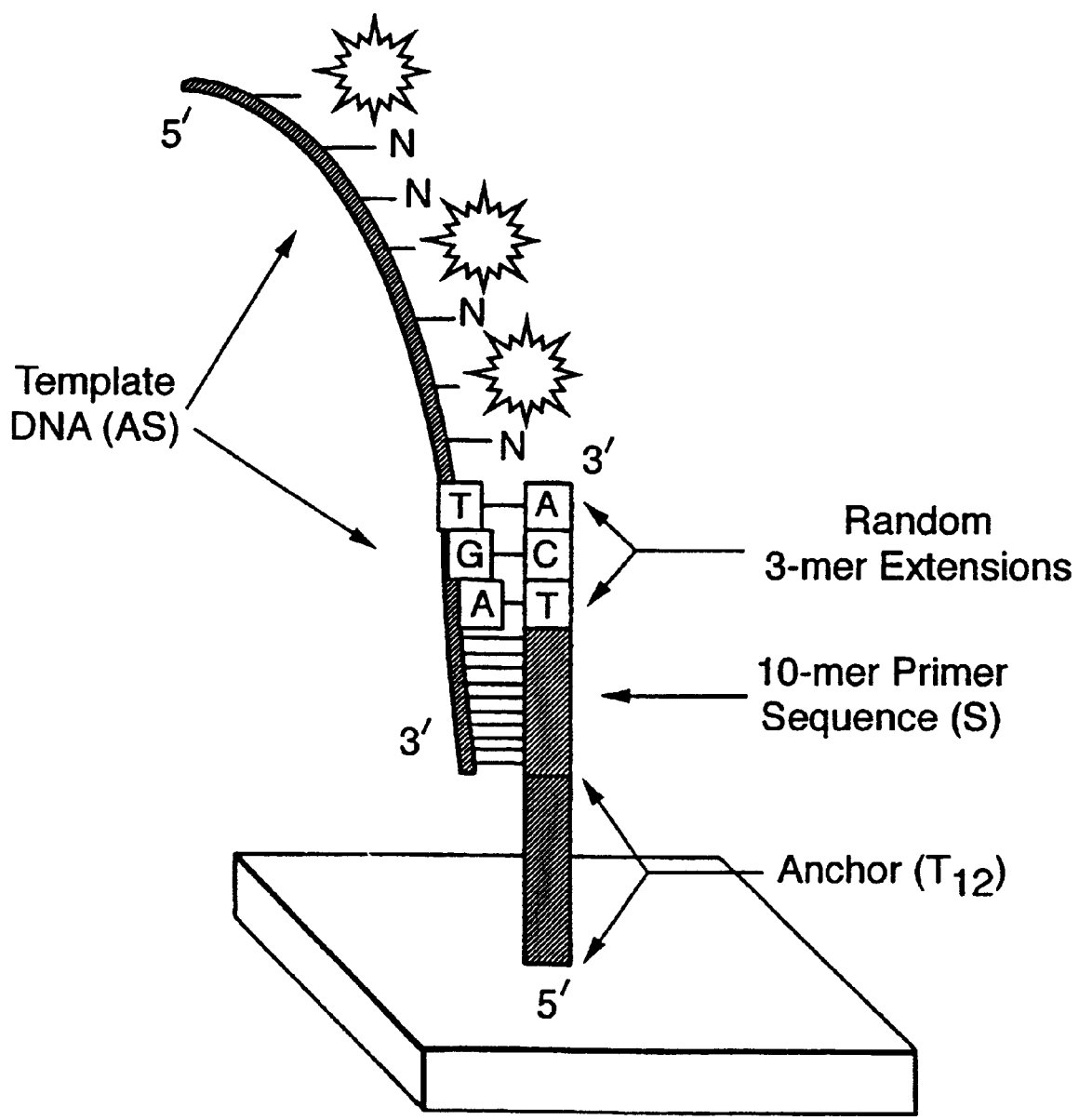
FIG. 1 depicts the general concept of the invention wherein a template DNA fragment has hybridized to an oligonucleotide probe and the oligonucleotide probe carries at its 3' end a random 3-mer extension.

The nucleic acid to be analysed may be genomic DNA or RNA e.g. mRNA of an organism such as a plant, animal, bacteria or virus. The method is expected to be useful for applications where RAPD analysis is currently used, including gene mapping, detection of strain diversity, population analysis, epidemiology, the demonstration of phylogenetic and taxonomic relationships, and gene expression studies.

In step a) the nucleic acid to be analysed is amplified using a single primer (or possibly several primers) in a low stringency amplification reaction e.g. by PCR. This primer is a chain of units capable of hybridising in a substantially sequence-specific manner to a suitable chain of the nucleic acid to be analysed; to form a hybrid in which the primer chain is capable of enzymatic chain extension. The primer is composed of units which are either nucleotides or nucleotide analogues.

Generally speaking, a nucleotide analogue is a compound which is capable of being incorporated in a chain of nucleotide residues; and which is capable of hybridising in a more or less base-specific manner with a base of a complementary nucleic acid chain; and which may be a substrate for chain-extending enzymes. A nucleotide analogue may be a nucleotide modified: in the base, e.g. so as to affect base-pairing properties; and/or in the sugar or backbone moiety, e.g. as in ddNTPs and in the amide linked backbones of PNA; and/or in the phosphate moiety.

For the primers for this invention, peptide nucleic acids are of interest. Preferably however the primer is an oligonucleotide. The primer preferably has from 7–40 residues. Usually a short primer with 8–10 residues is used, but primers with up to 20 or 40 residues are also possible. After amplification, all amplimers will have the same sequence at both ends, the length of that sequence depending on the primer.

In many techniques where amplification is involved, there is a need for standardised reagent supply. For this purpose it may be convenient to use Ready-To-Go™ (RTG) RAPD beads marketed by Amersham Pharmacia Biotech which provide the reagents for the reactions. The RTG RAPD beads contain thermostable polymerases, dNTPs, BSA and buffer for a 25 μl reaction.

Preferably the amplified nucleic acid is broken into fragments. Fragmentation is preferred because only small fragments may have access to a probe bound on a solid support. In the examples below, two different approaches have been used, restriction enzymes and the enzyme uracil-DNA-glycosylase (UDGase). To use UDGase, dUTP must be added to the amplification mix. UDGase activity is blocked by a UDGase inhibitor. Other enzymatic, chemical and physical methods of breaking the amplified nucleic acid are known and may be used.

An important feature of this invention is the use of an array of immobilised probes. These are herein called probes, although they also act as primers for chain extension. Each immobilised probe comprises a primer sequence that is identical to (or complementary to) the sequence of the primer used in a). Each probe also comprises an adjacent sequence, generally of 1–8 nucleotide (or nucleotide analogue) residues. The adjacent sequence of each probe of the array is different from that of every other probe of the array. Preferably the array consists of a complete set of probes having adjacent sequences of a particular length, that is to say: four probes where each adjacent sequence is 1 nucleotide residue; or 16 probes where each adjacent sequence is 2 nucleotide residues; or 64 probes where each adjacent sequence is 3 nucleotide residues; or $4^n$ probes where each adjacent sequence is n nucleotide residues.

Preferably the adjacent sequence is positioned at the 3'-end of the primer sequence of the probe. Preferably the probe is tethered to a support through the 5'-terminal residue of the primer sequence, either covalently or by means of strong binding agents such as the streptavidin-biotin system.

In step c), the fragments of the amplified nucleic acid from a) are applied under hybridisation conditions to the array. Because all probes of the array include a primer sequence complementary to the primer-derived sequence of the amplified nucleic acid, hybridisation takes place at every probe location of the array.

In step d) template-directed chain extension of probes of the array is effected. Preferably this chain extension is performed using a polymerase enzyme together with a supply of nucleotides or nucleotide analogues. Under these circumstances, chain extension only takes place where the nucleotide residues at the 3'-end of the probe accurately match those of the hybridised nucleic acid fragment.

For this purpose a nucleotide analogue may have a base analogue that is degenerate, by having the ability to base pair with two or three of the natural bases, or universal, by forming base pairs with each of the natural bases without discrimination. Also, chain-terminating ddNTPs may be used as nucleotide analogues, and are preferred.

Nucleotides or nucleotide analogues for addition during the chain extension step may be labelled for ease of detection. The nature of the label is not material to the invention. Examples are radioisotopes, fluorescent moieties, haptens, and components of chromogenic or chemiluminescent enzyme systems. Preferably the four ddNTPs are used, each labelled with a different fluorescent or other label, so that the four different signals can be read simultaneously.

Step e) of the method involves observing the location of probes of the array when chain extension has taken place in d). This observation can be made by standard means using the one or more labels added during chain extension. The result is a pattern which is characteristic of the nucleic acid being analysed.

In another aspect the invention provides a nucleic acid analysis kit comprising:

i) a primer for amplifying a nucleic acid,
ii) an array of probes in which each probe comprises a primer sequence that is identical to (or complementary to) the sequence of the primer, and an adjacent sequence which is different in each probe of the array,
iii) and reagents for effecting enzymatic chain extension of nucleic acid hybrids.

Description of the Ordered Arrangement of an Array of Oligonucleotide Probes

An oligonucleotide primer typically has 7 to 40 nucleotides; for example with 10 nucleotides: 5'-NNNNNNNNNN-3'-OH. Oligonucleotide probes generally comprise oligonucleotide primers and an additional 1–8 bases; for example with 2 additional bases a total of 16 ($4^2$) probes are needed:

NNNNNNNNNNAA NNNNNNNNNNCA
NNNNNNNNNNAC NNNNNNNNNNCC
NNNNNNNNNNAG NNNNNNNNNNCG
NNNNNNNNNNAT NNNNNNNNNNCT
NNNNNNNNNNGA NNNNNNNNNNTA
NNNNNNNNNNGC NNNNNNNNNNTC
NNNNNNNNNNGG NNNNNNNNNNTG
NNNNNNNNNNGT NNNNNNNNNNTT for 3 additional bases $4^3$=64 probes are needed, etc. up to $4^8 \approx 65,000$.

After hybridisation and extension of an array of 64 probes, two different patterns can look like this;

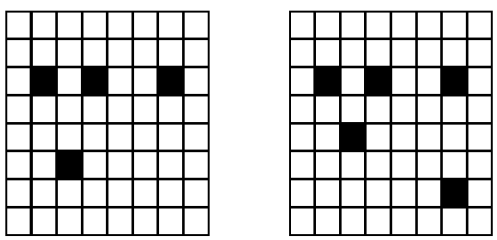

Reference is directed to the accompanying drawings, in which:

FIG. 1 illustrates the principle of the invention. A template DNA fragment has a 10-mer oligonucleotide primer at its 3' end. An oligonucleotide probe has been immobilised on a surface of a support through a $T_{12}$ anchor joined at the 5'-end of (the complement of) the 10-mer oligonucleotide primer sequence. The oligonucleotide probe carries at its 3'-end a random 3-mer extension, in this case TCA.

The template DNA fragment has hybridised to the oligonucleotide probe. By chance the sequence of the template DNA (AGT) complements the 3-mer extension at the 3'-end of the oligonucleotide probe. As a result, template-directed chain extension of the oligonucleotide probe has taken place, and a total of seven nucleotides (N) or labelled nucleotide analogues (*) have been added to its 3'-end.

Figure 2:
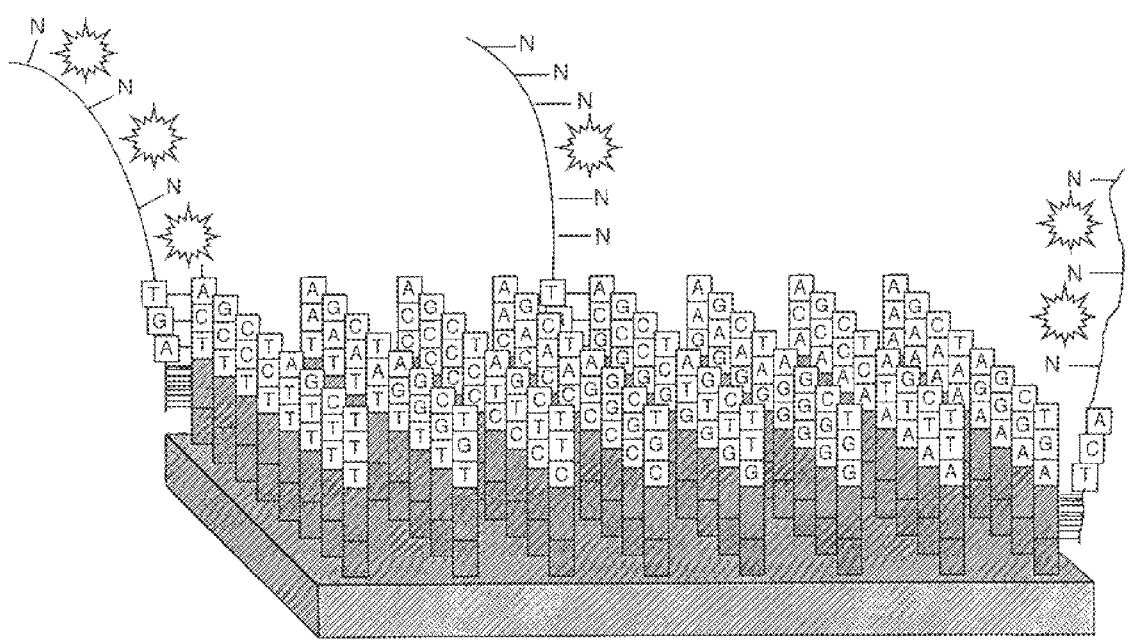
FIG. 2 depicts an array of oligonucleotide probes together with three fragments of template DNA where hybridisation and chain extension have taken place.

FIG. 2 is a corresponding diagram showing an array of oligonucleotide probes, together with three fragments of template DNA where hybridisation and chain extension have taken place.

FIG. 3 shows bacterial genotyping data obtained in Example I on two different strains of E. coli using three different primers.

Figure 4I:
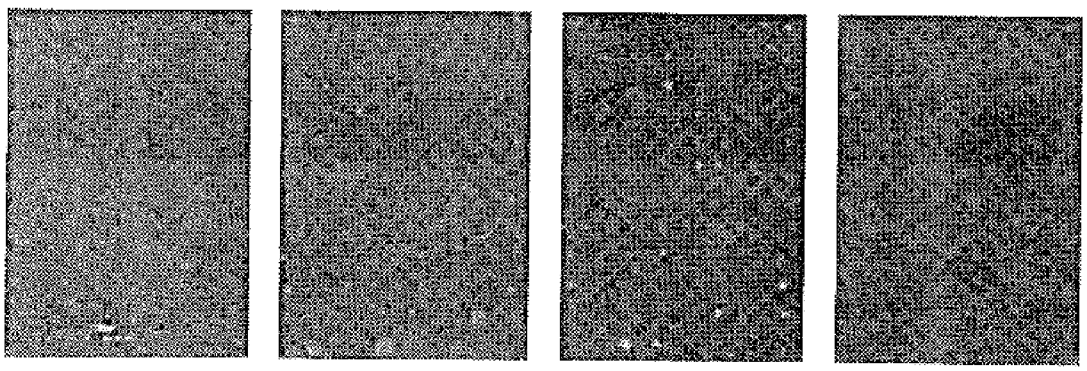
FIG. 4(*i–vi*) depicts the total internal reflection fluorescence (TIRF) data for six Listeria strains obtained by practice of the methods of the invention.
Figure 4:
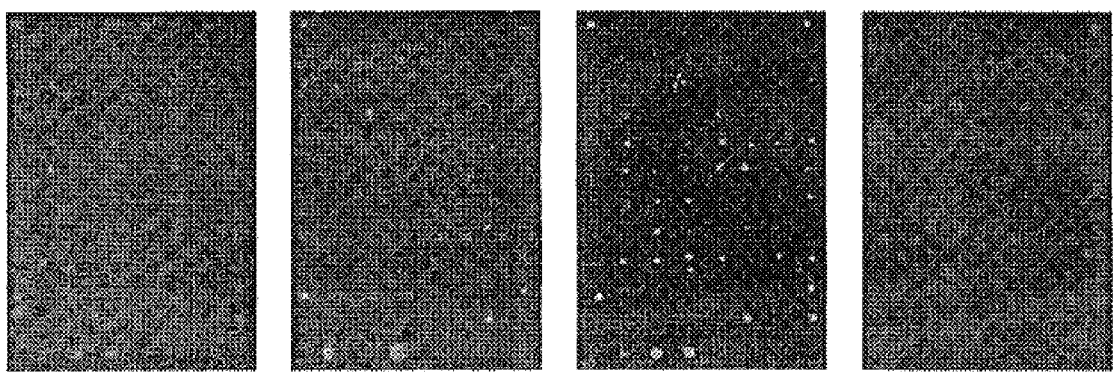
Figure 4:
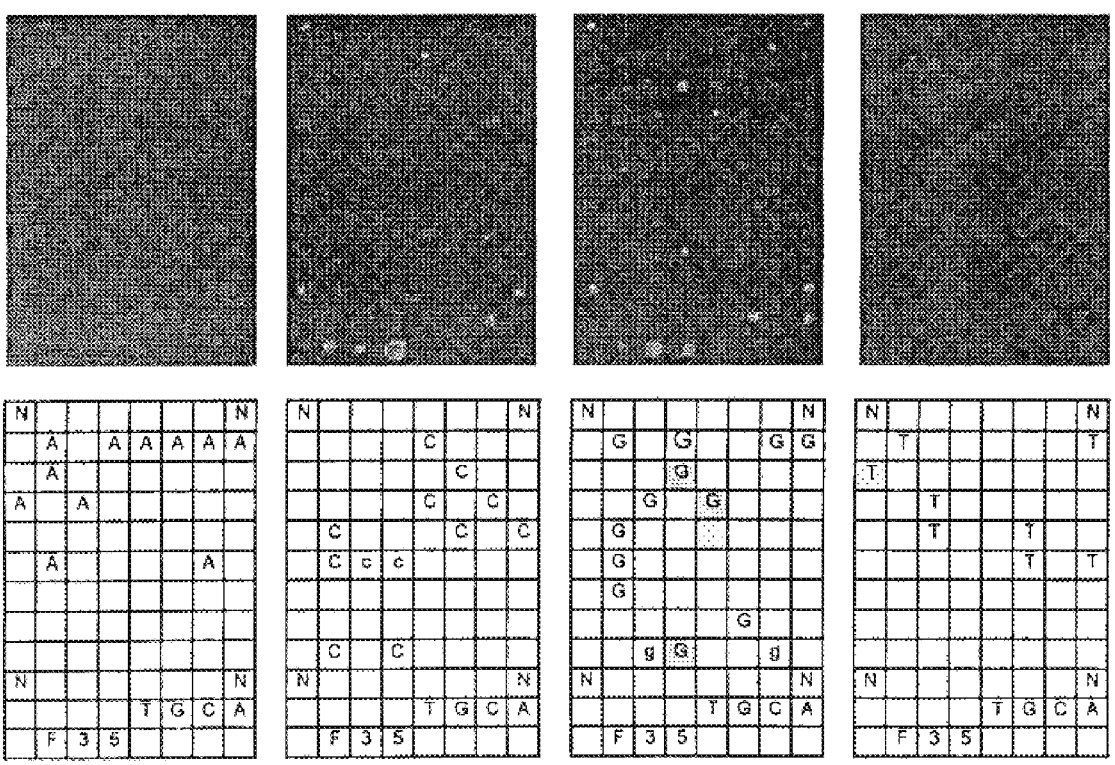
Figure 4V:
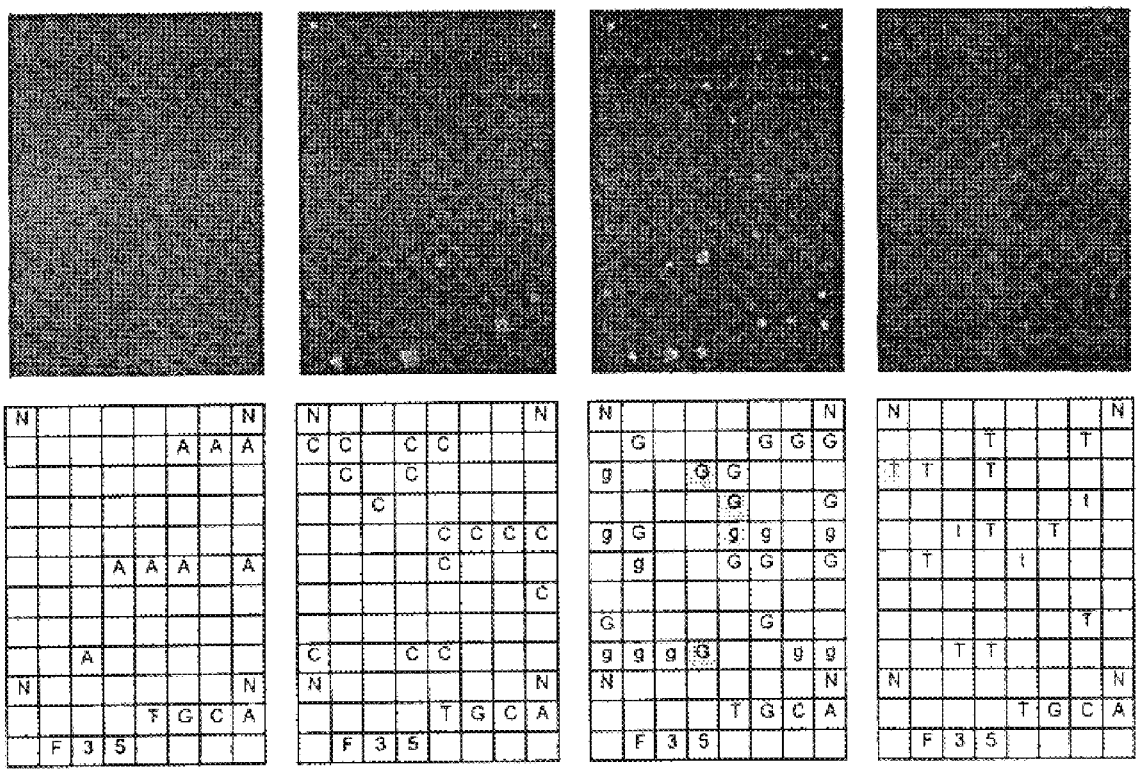
Figure 4:
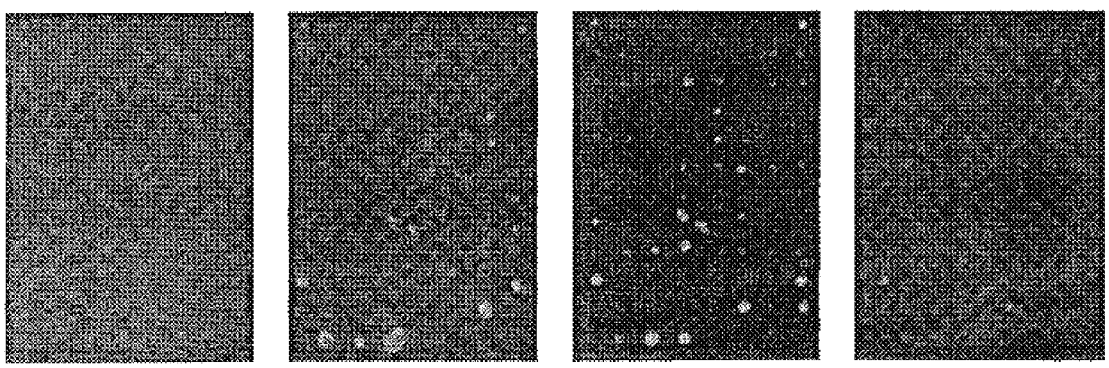

FIG. 4(i–vi) shows TIRF data obtained on six different strains of Listeia in Example 3. For each strain, the upper four panels show images obtained with four different labelled ddNTPs; and the lower panels show the data expressed graphically (capital letters are strong signals, lower case letters are weak signals).

Figure 5:
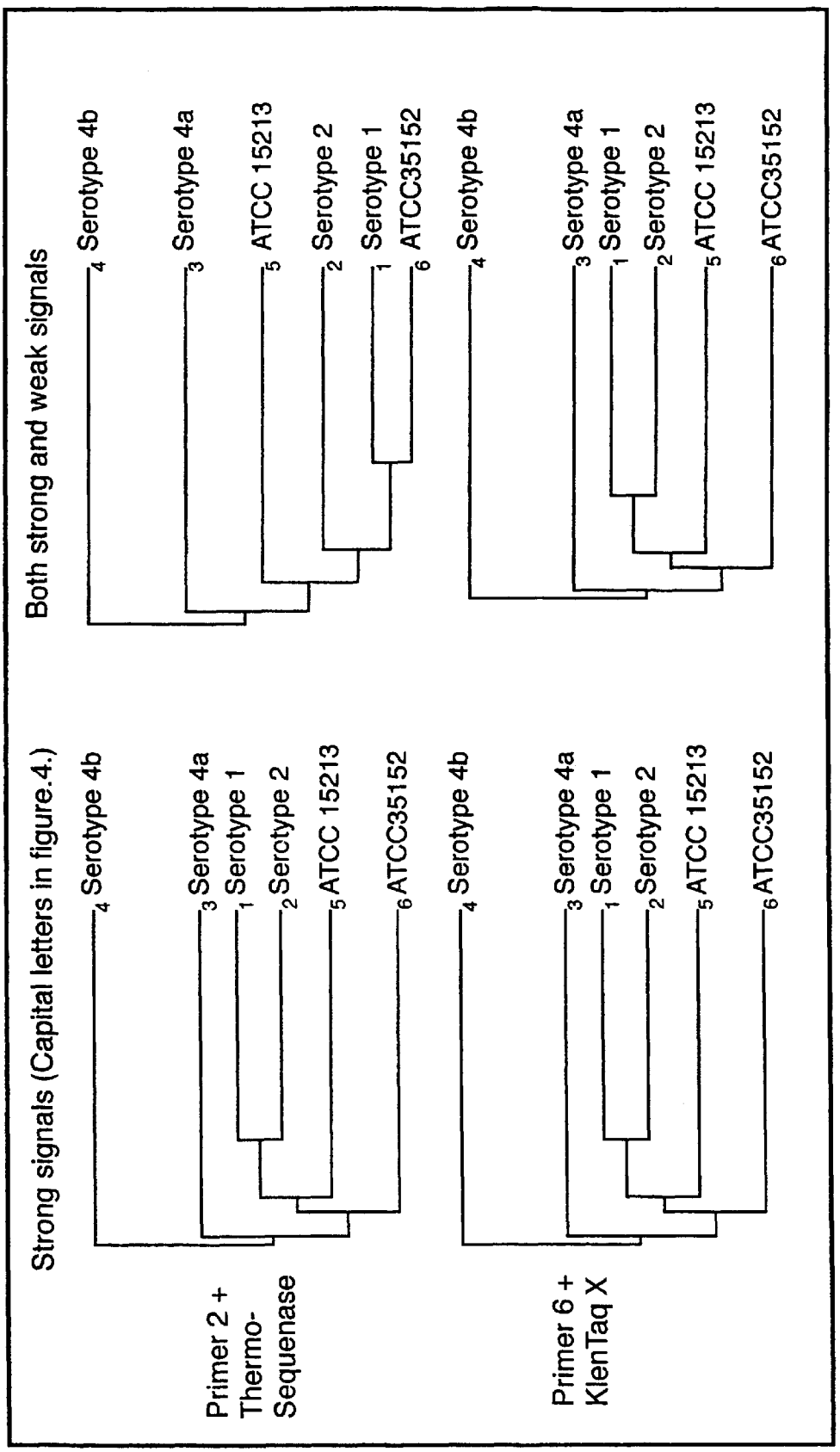
FIG. 5 depicts four dendrograms illustrating the Listeria data of FIG. 4(*i–vi*).

FIG. 5 comprises four dendograms and contains a comparison between strong and weak assigned spots from the images. Primer 2 was compared with primer 6 amplified Listeria DNA in combination with two polymerase enzymes.

In the examples below, the acronym RAPX is used to denote the method of the present invention comprising a combination of the random amplified polymorphic DNA (RAPD) and arrayed primer extension (APEX) techniques.

EXAMPLES

The first example shows the invention method performed in microtitre plates (MTP) with both fluorescein labelled dCTP and anti-fluorescein antibodies and detected by using para-nitrophenyl phosphate (pNpp). Two different bacterial DNA were used in order to show that different patterns could be generated.

The second example shows the method performed on a microscope slide with one of the bacterial DNA as template.

Fragmentation is an important step because only small fragments will have access to the bound primer on the solid support. For this step two different approaches were used, restriction enzyme cleavage and using the enzyme Uracil-DNA-glycosylase (UDGase). To use UDGase, dUTP must be added to the amplification mix. UDGase activity is blocked by a UDGase inhibitor.

The whole procedure consists of the following steps:
RAPD amplification
Digestion/Fragmentation
Purification and quantification
Array setup on chip or MTP
Hybridisation and chain extension
Detection of reacted products Example 1

Genomic DNA was purified from E. coli strains according to standard protocols. Test DNA from Pharmacia Biotech RTG™ RAPD kit was used.
RAPD Amplification:
Each DNA was amplified generally according to the manufacturer's protocol and with the RTG RAPD beads. One reaction contained 25 pmol primer, 10 ng bacterial DNA and water to 25 µl.
Primers:
Primer 2: GGTGCGGGAA (SEQ ID NO:1)
Primer 6: CCCGTCAGCA (SEQ ID NO:2)
Primer 1283: GCGATCCCCA (SEQ ID NO:3)
Escherichia coli strains: BL21 and C1a
When large quantities of RAPD templates are needed several batches of the same sample were amplified, following the prescribed RAPD protocol.

| Number of Cycles | Temp | Time |
|---|---|---|
| 1 cycle | 50° C. | 8 minutes |
| 1 cycle | 95° C. | 3 minutes |
| 45 cycles | 95° C. | 1 minute |
|  | 36° C. | 1 minute |
|  | 72° C. | 2 minutes |
| 1 cycle | 35° C. | 30 minutes |

Five microlitre of material from each tube were tested on a polyacrylamide gel.
Digestion
The generated RAPD products were fragmented according to two different methods, restriction enzyme cleavage or using the enzyme UDGase.
Cleavage with Restriction Enzymes
The RAPD product (DNA) was cleaved with Alu1 and Hha1.

| Ingredient | 1 Tube |
|---|---|
| Sterile water | 240 µl |
| Restriction Buffer | 40 µl |
| Alu1 Enzyme (3.5) | 25 µl (75 units) |
| RAPD product (DNA) | 95 µl |
| TOTAL | 400 µl |

Incubate tubes for 1 hour in a 37° C. oven.
Place 100 µl of the following master mix in each tube:

| Ingredient | 1 Tube |
|---|---|
| Sterile water | 15 µl |
| Restriction Buffer | 60 µl |
| Hha 1 Enzyme (3.6) | 25 µl (75 units) |
| TOTAL | 400 µl |

Incubate for 2 hours in a 37° C. oven.
After cleavage 5 µl was tested on a polyacrylamide gel.
Cleavage with UDGase Bacterial DNA was amplified with an addition of 80 mM dUTP before treatment with UDGase and UDGase inhibitor (UDI).

One RAPD reaction contained 25 pmol primer, 10 ng bacterial DNA, 80 mM dUTP (Pharmacia Biotech), water to 25 µl and one RTG RAPD bead, with the same amplification conditions as above.

UDGase Treatment, Set Up:

25 µl RAPD DNA
6.25 µl UDGase (1 U/µl New England Biolabs)
6.25 µl 10×UDGase mix
25 µl water
Incubate at 37° C. for 24 min.
Add 6.25 µl UDI
Incubate at, at least 75° C., for 10 minutes and test on polyacrylamide gel.

Purification and Quantification

Cleaved RAPD products were concentrated with a Centricon-10 Concentrator. The concentrated DNA was then filtered through an Amicon EZ filter to remove excess of primers, free nucleotides and enzymes.

Finally, the DNA concentration was measured using Optical Density at 260 nm and 280 nm using spectrophotometer and calculate the volume to get 2.5 µg DNA for the hybridisation and extension reactions.

Preparation of Array Plates

Three sets of 64 oligonucleotides with primer sequences from primers 2, 6 and 1283 extended with all possible combinations of three additional nucleotides (nt), giving them a total length of 13 nt, were bound to microtitre plate wells.

Reactions in Wells

RAPD DNA template (2.5 µg) was added to each well and heated to boiling temperature for 3 minutes.

| Order | Component | Volume - 1 well |
|---|---|---|
| 1 | water | 79.2 µl |
| 2 | 5x TSP buffer | 20 µl |
| 3 | Deoxy Mix | 0.1 µl |
| 4 | Fl-dCTP (.5 mmol) | 0.2 µl |
| 5 | Tba Polymerase | 0.5 µl |
|   | Total | 100 µl |

Tba Polymerase is a DNA polymerase from the bacterium *Thermococcus barrossi*.

After adding the reaction mix, incubate at 72° C. for 45 minutes in a large oven.

5× Thermostable Polymerase Reaction Buffer (TSP)

| Component | Volume | [Final] |
|---|---|---|
| 1M Tris-HCl, pH 9.5 | 10 µl | 100 mM |
| 1M MgSO$_4$ | 5 µl | 50 mM |
| 10% Triton X-100 | 25 µl | 2.5% |
| Milli Q ™ water | 60 µl | |
| | 100 µl | |

Mix. Sterile filter. Store at room temperature.

dNTP (Deoxy) Mix (dA, dG, & dT)

| Component | Volume | [Final] |
|---|---|---|
| 100 mM dATP | 5 µl | 1 mM |
| 100 mM dGTP | 5 µl | 1 mM |
| 100 mM dTTP | 5 µl | 1 mM |
| Milli Q ™ water | 485 µl | |
| | 500 µl | |

Store at −20° C.

Detection of Reaction Products

In order to enhance the signal, anti-fluorescein antibodies labelled with alkaline phosphatase were used. Before detection of the reaction, each well was blocked with a buffer containing bovine serum albumin. One hundred microlitre of anti-fluorescein antibody solution was pipetted in to each well and incubated 60 minutes at room temperature. The microtitre plate was washed several times before para-nitrophenyl phosphate reagent was added and a yellow colour was developed at room temperature.

The yellow signal output read from each well is a quantitative measure on the amount of the RAPD fragment for that particular RAPD-extended probe. All data from the reader (Spectra Max 3000) was used for generation of a graph for each organism, FIG. 3.

This is a set of overlaid duplicate optical density readings. Signals have been determined by high values that have consistently shown up through four experiments that have compared these two strains of bacteria.

In the centre is a bar code that represents signals for the two strains.

Example 2

This experiment was performed to show that the method of the invention also works when the array of oligonucleotide probes is on a glass surface. For this purpose, silanised glass slides were procured and three sets of the three oligonucleotide probe families of Example 1 (3×64=192 probes) were synthesised to have amino-linked 5'-modified ends. These oligonucleotide probes were spotted on to the silanised surface of the glass slide, the experiment being performed in triplicate. Border controls (self-extending oligonucleotides capable of A, G, T or C addition) were spotted in a pattern that surrounded each of the four spotted grids.

Nucleic acid template material was prepared, as described in Example 1, starting from genomic DNA of the *E. coli* strain BL21. Template material was validated by running samples on polyacrylamide gel and staining with ethidium bromide. It was found that the material digested with the mixture of frequent cutting enzymes (Alu1 and Hha1) seem to average about 250 bp in size (50–500 bp range).

Hybridisation and extension reactions were performed generally as described in Example 1. The extension reaction mix was:

13.5 µl RAPD DNA fragments (2 pmol)
1 µl 17.5×Thermosequenase DNA polymerase buffer
1 µl unlabelled dNTPs (50 mM)
1 µl Cy5-ddCTP (50 mM)
1 µl Thermosequenase DNA polymerase (5 U/µl)

Incubate at 65° C. during 20 minutes. The Cy5-ddCTP was a sulphonated cyanine dye dideoxy nucleotide marketed by Dupont. Control reactions were first performed in order to ensure the presence of correctly spotted oligonucleotides and validate a successful enzyme reaction. In the presence of polymerase enzyme without any template, only the border controls appeared. The addition of three different oligonucleotides that would specifically hybridise to one of each of the primer families, resulted in the detection of the appropriate spots in the array. These control experiments demonstrated the ability to perform specific reactions on the microscope slide surface.

Template nucleic acid material (prepared as described in Example 1) that represents sequence information of the bacterial genome BL21 was then applied to the oligonucleotide probe array. Using a total internal reflection detection system, a specific pattern of signals was seen for template material from the BL21 source.

Example 3

Amplification:
   Bacterial DNA: E. coli BL21 and E. coli C1a strains are from the Amersham Pharmacia Biotech RTG RAPD kit. Six Listeria monocytogenes strains are Listeria monocytogenes; serotype 1, serotype 2, serotype 4a, serotype 4b, ATCC 15313 and ATCC 35152.
   Primers: Primer 2, 6 are from the Amersham Pharmacia Biotech RTG RAPD kit and primer 1283 is from Berg et al.
   Amplification reagents: RAPD RTG beads from the Amersham Pharmacia Biotech RTG RAPD kit.
   All samples were spiked with one microliter 2.5 mM dUTP
Enzymes for Fragmentation of RAPD Products:
   Shrimp alkaline phosphatase (SAP)1 U/μl APB.
   Uracil-DNA-glycosylase, (if from PE UDG=UNG) 1 U/μl NE
Biolabs
   SAP will degrade (dephosphorylate) all free dNTPs and UDG will remove all dU from the DNA and after heating the strands will be broken at these points. This step is applicable to any DNA fragment.
Primers for Spotting:
   All 192 primers were 25-mers with an amino-activated 5'-end.
   The general sequence for the primers is
   5'-NH$_4$-TTT TTT TTT TTT-P-N$_1$N$_2$N$_3$-3', where P is the primer sequence from Primer 2, Primer 6 or Primer 1283; and N$_{1-3}$ is A, C, G or T. (See: SEQ ID NO: 5; SEQ ID NO: 6; and SEQ ID NO: 7).
   For the arrangements of the primers see below.
   In Primer 2 set up P=GTTTC GCTCC (SEQ ID NO: 4), Primer 6 set up P=CCCGT CAGCA (SEQ ID NO: 2), and in Primer 1283 set up P=GCGAT CCCCA (SEQ ID NO: 3).

| N | | | | | | | N |
|---|---|---|---|---|---|---|---|
| T$_{12}$P-TGA | T$_{12}$P-TAA | T$_{12}$P-GGA | T$_{12}$P-GAA | T$_{12}$P-CGA | T$_{12}$P-CAA | T$_{12}$P-AGA | T$_{12}$P-AAA |
| T$_{12}$P-TGC | T$_{12}$P-TAC | T$_{12}$P-GGC | T$_{12}$P-GAC | T$_{12}$P-CGC | T$_{12}$P-CAC | T$_{12}$P-AGC | T$_{12}$P-AAC |
| T$_{12}$P-TGG | T$_{12}$P-TAG | T$_{12}$P-GGG | T$_{12}$P-GAG | T$_{12}$P-CGG | T$_{12}$P-CAG | T$_{12}$P-AGG | T$_{12}$P-AAG |
| T$_{12}$P-TGT | T$_{12}$P-TAT | T$_{12}$P-GGT | T$_{12}$P-GAT | T$_{12}$P-CGT | T$_{12}$P-CAT | T$_{12}$P-AGT | T$_{12}$P-AAT |
| T$_{12}$P-TTA | T$_{12}$P-TCA | T$_{12}$P-GTA | T$_{12}$P-GCA | T$_{12}$P-CTA | T$_{12}$P-CCA | T$_{12}$P-ATA | T$_{12}$P-ACA |
| T$_{12}$P-TTC | T$_{12}$P-TCC | T$_{12}$P-GTC | T$_{12}$P-GCC | T$_{12}$P-CTC | T$_{12}$P-CCC | T$_{12}$P-ATC | T$_{12}$P-ACC |
| T$_{12}$P-TTG | T$_{12}$P-TCG | T$_{12}$P-GTG | T$_{12}$P-GCG | T$_{12}$P-CTG | T$_{12}$P-CCG | T$_{12}$P-ATG | T$_{12}$P-ACG |
| T$_{12}$P-TTT | T$_{12}$P-TCT | T$_{12}$P-GTT | T$_{12}$P-GCT | T$_{12}$P-CTT | T$_{12}$P-CCT | T$_{12}$P-ATT | T$_{12}$P-ACT |
| N | | | | T | G | C | N A |
| | Cy2 | Cy3 | Cy5 | | | | |

A is a self extended primer that only extends with A;
C is a self extended primer that only extends with C;
G is a self extended primer that only extends with G;
T is a self extended primer that only extends with T;
N is a mix of A, C, G, and T, self extending primers.
Cy2, Cy3 and Cy5 are pre-labelled primers with respectively dye. (Can also be self extended in some cases.)

Extension Reagents for the APEX Reaction
   Dyes:

| | |
|---|---|
| Cy2 - ddCTP (equal to fluorescein) | 50 μM |
| Cy3 - ddGTP | 50 μM |
| Cy3 - ddATP | 50 μM |
| Cy5 - ddUTP (often written as T in many of the reactions and results) | 50 μM |

Dye mixes may vary from time to time, use normal stocks of 50 μM.
      10×ThermoSequenase DNA polymerase buffer (TS): 260 mM Tris-HCl pH 9.5; 65 mM MgCl$_2$, this buffer does not have high influence on the APEX reaction.
      ThermoSequenase DNA polymerase (from Amersham Pharmacia Biotech (APB)) 4 U/μl. If needed dilute with T.S. dilution buffer (=10 mM Tris-HCl pH 8.0; 1 mM β-mercaptoethanol, 0.5% Tween-20 (v/v), 0.5% Nonidet P-40 (v/v)).
      KlenTaq X DNA polymerase (WO 92/06188 with the same mutation for improved ddNTP incorporation as in Thermosequenase DNA polymerase) ~5 U/μl.

Methods
Preparation of Glass Slides Before Spotting of Primer:
1. Arrange 25–30 cover slips (24×60 mm) in a stainless staining tray.
2. Immerse the tray in glass staining dish with acetone to fully immerse slides.
3. Place the glass staining dish in sonicator for 10 minutes.
4. Remove the tray from acetone bath, shake off excess of acetone and rinse several times (at least twice) in MilliQ water.
5. Immerse tray in 100 mM NaOH and sonicate for 10 minutes (a few more minutes, no problem).
6. Remove the tray and shake off the excess of NaOH and rinse several times (at least twice) in MilliQ water.
7. Immerse tray in silane solution and sonicate for 2 minutes.
8. Wash slides by immersion in 100% EtOH once. (Silane and silane contaminated EtOH in special container for silane discharge.)
9. Dry the tray with the slides in nitrogen with a high velocity (without breaking the slides).
10. Cure the slides in a vacuum oven at 100° C. over night or until they are used for spotting (at least 20 minutes vacuum is not needed).
Spotting of Oligos:
   All spotting was done with a lab made spotter with 96 parallel capacity. Each slide was spotted with three replicas of the primers.
   After spotting the slides were allowed to air dry for 5 to 15 minutes, when dried and marked. They were stored at room temperature, in a dry place, in the trays until used. Chips can be used for a few weeks, probably longer. Arrangements of oligos and sequences see above.

RAPD Amplification

The RAPD amplification were done according to the Ready-To-Go RAPD instruction. After 45 cycles (96° C., 1 min.; 36° C., 1 min.; 72° C., 2 min.), one microliter of the products was tested on a 4–20% premade PAGE, before the fragmentation step.

Fragmentation of RAPD (DNA fragment) Products:

Before RAPX (APEX) can be done all DNA fragments must be fragmented so all new fragments can get access to the primer on the chip.

Set Up:

20 µl DNA from RAPD reaction 0.5 µl SAP (Shrimp alkaline phosphatase) 1 U/µl 0.5 µl UDG (Uracil-DNA-glycosylase, if from PE UDG× UNG)

1 U/µl NE Biolabs

Total: 21 µl

Incubate 37° C. for 1 hour.

Inactivate enzymes at 100° C. for 10 minutes.

The samples can now be frozen and stored until they are used.

Extension Method for the APEX Reaction Slide Treatment:

Start with washing the slides in hot water (90–98° C., not boiling) for 2×5 minutes in a 50 ml Falcon tube. When the slides are ready, remove them from the tube with a forceps and place them on a dry heater block at 48° C. The slide (DNA chip) is now ready for adding the reactions.

RAPX Reactions Set Up:

1. 4–5 µl DNA from RAPD reaction (or from PCR reaction if an APEX slide has been used). Note that the DNA must be fragmented before this step.
2. 3µl 10×TS buffer (the rest of the buffer comes from PCR and DG cleavage)
3. Water to 38 µl for dry-down method or 18 µl for cover slip method.
4. Heat denature at 100° C. for 7–10 minutes, target 8 minutes, not longer.
5. Spin the tube quickly and add quickly
6. 1 µl ThermoSequenase DNA polymerase (4U)
7. 1 µl Dye-mix (up to three dyes at the same time and quick spin and load on the slide).

These three last steps must be done under 1 minute, in order not to let DNA fragments renaturate. If cover slips are used, each reaction needs 20 µl, but the dry-down method is preferred, where all 40 µl of the reaction is physically spread out over the primer array with help of the tip of a pipette tip.

8. Incubate at 48° C. for 20 minutes with cover slip. Alternatively, the so called dry-down method can be used were the spread mix is allowed to dry down until no trace of solution is seen. This takes about 8 minutes. The signals with cover slips were better and with lower background.
9. Wash with hot water for 2–5 minutes, 2 times.
10. Ready to read on TIRF instrument.

Detection

The detection system is a total internal reflection fluorescence (TIRF), where microscopic slides are placed on top of a prism with oil on to link a laser beam in to the glass slide. The system has five different wave lengths from five different lasers to vary between. In this experiment only three were used. To detect Cy2 a laser with 488 nm was used, for Cy3 a 532 nm and for Cy5 a 635 nm laser was used. Image related software was based on Image Pro Plus 3.0.

Results

RAPD Amplification

The RAPD amplification was done with RTG RAPD beads in order to use a standardised method for further high reproducibility. The amplified products were analysed on an ethidium bromide stained polyacrylamide gel. The only reference to compare with was the RAPD manual from APB with the different primers and the two E. coli stains. The expected bands were seen, and correspond very well. In summary, all DNA were nicely amplified except the Listeria DNA with primer 1283, which contained too much broken DNA.

RAPX Reaction with E. coli DNA

DNA from the two E. coli stains BL21 and C1a were amplified and fragmented. The extension reaction is quick to set up and analyse. The extension can be done in two ways, either with or without a cover slip. If a cover slip is used the background is lower and was mainly used in the typing reactions, see below. But, in the first set up, the dry down method with no cover slip was used, which resulted in some circular shaped background.

In the set up of primers positive controls were used, in each corner of the matrix a mix of primers were added that always will be extended if the DNA polymerase is active. Below the matrix self extendible primers for the different bases were placed together with Cy-dyed primers for laser control. A self extended primer is a primer that has complementarily to it self or a neighbour, which then can be extended. The neighbour is seen in the cases with the 64 primers and the other control primers are fold back self extenders. The different pre-labelled primers gave expected signals showing that the detector and the imaging system is working. Taken together this show that the DNA polymerase is active and that the system is working perfectly with all positive signals.

After RAPD amplification and fragmentation the two E. coli stains BL21 and C1 were analysed on Primer 2 RAPX chips. The two different E. coli strains show clearly two different patterns, accordingly these two E. coli strains can be separated. Both E. coli strains gave four bands after RAPD analysis on PAA. Each band has two ends with the sequence from the primer, the sequence further in is not known. Accordingly, totally 8 spots can light up on a RAPX chip. Three panels with E. coli DNA have about 13 stronger signals and the control with no DNA has five signals, this corresponds well with the expected 8 spots. The position of the spots can not be predicted unless each fragment is sequenced or the whole genome of the organism is sequenced.

Typing of Six Listeria Strains with RAPX.

With the good tests with E. coli DNA in mind, the next step was to test if different patterns can be generated from several different strains, six strains from Listeria monocytogenes were then selected. The chosen strains had been typed with RAPD and analysed on silver stained gels by C. Ko, Hoefer see below, which will make it easier to interpret the results from the RAPX analysis.

Before the typing started the following two tests were done, firstly check of primer chips for self-extendible primers. Secondly, test two different thermostable enzymes, ThermoSequenase DNA polymerase and KlenTaqX DNA polymerase. The comparison of different Listeria strains was finally done.

During the work two different thermostable DNA polymerases was used. The majority of reactions were done with ThermoSequenase DNA polymerase, but also KlenTaqX DNA polymerase were used. The new enzyme KlenTaqX DNA polymerase, which is smaller in size than ThermoSequenase DNA polymerase gave stronger signals and lower background, which also made it easier to assign the base on the extended primers. All spots, even the weak ones where informative in the cluster analysis with elongation with KlenTaqX DNA polymerase, when the clusters from Primer 2 and Primer 6 were compared.

Each sample was analysed two times using two different dye mix systems, since not all terminators are available with dyes with separated spectrum. The two dye mixes were Mix1: Cy2-ddCTP, Cy3-ddGTP, Cy5-ddATP and Mix2:, Cy2-ddCTP, Cy3-ddGTP, Cy5-ddUTP. Thus, each sample generated six images, but the assembly of these six images gave a pseudo four dye system, by choosing the best of either "2" or "4", and "3" or "5" to get C and G extendible primers, respectively. The A and T (ddUTP) extendible primers are from Cy5-labelled terminators, "1" and "6".

The next step was to test all Listetia strains in the RAPX reaction. It was notable how quick the RAPX analysis is done, even though the reaction was done in duplicate, with two different dye mix combinations. The RAPX reaction takes about 30 minutes, including pipetting, set up and reading the images.

For the analysis of relation between the different strains the best of the triplicate signals on each slide were selected. All signals shown on the image were scored manually and the extended bases were assigned. FIG. 4 shows all six Listefa strains after analysis with Primer 6, these samples were extended with KlenTaqX DNA polymerase. The same type of data was also generated from Primer 2, but with ThermoSequenase DNA polymerase, data not shown. All assigned bases were stored in a spread sheet software for cluster analysis, which was done in two steps. In the first step all assigned bases were converted to figures and then a similarity table was calculated. Finally a dendogram was calculated as shown in FIG. 5.

When cluster data from a poster made by Chris Ko at Hoefer Pharmacia in San Francisco were compared with the data generated with RAPX, the similarities are seen. Then the dendograms from Primer 6 and 2 data were compared with the dendogram generated by Chris Ko and were shown to be very similar. The small differences could be explained by the use of different primers in C Ko's experiments.

Conclusions

The RAPX method is shown to be a quick and accurate method. It takes approximately 30 minutes to perform the extension, and detection including hands on time and incubations. Different strains can be analysed with the RAPX method and the same cluster/groups can be identified when compared with ordinary gel electrophoresis. The speed and the easiness of the RAPX method guarantee for the future use of this array technology in bacterial typing as well as relationship studies of other organisms. An array format like this method could easily be highly automated.

What is claimed is:

1. A nucleic acid analysis method which comprises:
   a) using a primer to amplify the nucleic acid,
   b) providing an array of probes in which each probe comprises a primer sequence that is identical to or complementary to the sequence of the primer, and an adjacent sequence which is different in each probe of the array,
   c) applying the amplified nucleic acid from a) under hybridisation conditions to the array of b),
   d) effecting enzymatic chain extension of any probe where the adjacent sequence matches that of the hybridised amplified nucleic acid, and
   e) observing the location of probes of the array where chain extension has taken place in d).

2. The method as claimed in claim 1, wherein the nucleic acid is genomic DNA of an organism.

3. The method as claimed in claim 1, wherein the primer is an oligonucleotide primer having 7–40 nucleotide residues.

4. The method as claimed in claim 1, wherein the amplified nucleic acid in a) is broken into fragments.

5. The method of claim 4, wherein a dUTP/uracil-DNA-glycosylase system is used to break the amplified nucleic acid into fragments.

6. The method of claim 1, wherein the adjacent sequence of each probe of the array contains 1–8 nucleotide residues.

7. The method as claimed in claim 1, wherein different probes of the array occupy different cells on a surface of a support.

8. The method as claimed in claim 1, wherein each probe is immobilised at its 5'-end.

9. The method as claimed in claim 1, wherein each probe comprises a primer sequence and an adjacent sequence positioned at the 3'-end of the primer sequence.

10. The method as claimed in claim 1, wherein chain extension is performed in d) using a polymerase enzyme.

11. The method as claimed in claim 1, wherein chain extension is performed in d) using labelled nucleotides or labelled nucleotide analogues.

12. The method as claimed in claim 11, wherein the labelled nucleotides or labelled nucleotide analogues are labelled dideoxynucleotides.

13. The method of claim 12 wherein four dideoxynucleotides, each labelled with a different fluorescent label, are used.

14. The method as claimed in claim 1, wherein in step e) a pattern of locations is observed and used to compare nucleic acids from one organism with those from another organism.

15. A nucleic acid analysis kit comprising:
   i) a primer for amplifying a nucleic acid, and
   ii) an array of probes in which each probe comprises a primer sequence that is identical to or complementary to the sequence of the primer, and an adjacent sequence which is different in each probe of the array.

16. The nucleic acid analysis kit of claim 15 comprising also one or more of:
   iii) reagents for amplifying a nucleic acid,
   iv) reagents for fragmentation of an amplified nucleic acid,
   v) and reagents for effecting enzymatic chain extension of nucleic acid hybrids.

* * * * *

SEQUENCE LISTING

<160> NUMBER OF SEQ ID NOS: 7

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: primer 2

<400> SEQUENCE: 1
ggtgcgggaa                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: primer 6

<400> SEQUENCE: 2
cccgtcagca                                                                10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: primer 1283

<400> SEQUENCE: 3
gcgatcccca                                                                10

<210> SEQ ID NO 4
<211> LENGTH: 10

```
<212> TYPE: DNA
<213> ORGANISM: Artificial Sequence
<220> FEATURE:
<223> OTHER INFORMATION: Description of Artificial Sequence: primer

<400> SEQUENCE: 4
gtttcgctcc                                                              10

<210> SEQ ID NO 5
<211> LENGTH: 25
<212> TYPE: DNA
<213> ORGANISM: Artificial Sequence
<220> FEATURE:
<221> NAME/KEY: misc_feature
<222> LOCATION: (23)..(25)
<223> OTHER INFORMATION: N= A, C, G, or T
<223> OTHER INFORMATION: Description of Artificial Sequence: primer

<400> SEQUENCE: 5
tttttttttt ttgtttcgct ccnnn                                             25

<210> SEQ ID NO 6
<211> LENGTH: 25
<212> TYPE: DNA
<213> ORGANISM: Artificial Sequence
<220> FEATURE:
<221> NAME/KEY: misc_feature
<222> LOCATION: (23)..(25)
<223> OTHER INFORMATION: N= A,C,G or T
<223> OTHER INFORMATION: Description of Artificial Sequence: primer

<400> SEQUENCE: 6
tttttttttt ttcccgtcag cannn                                             25

<210> SEQ ID NO 7
<211> LENGTH: 25
<212> TYPE: DNA
<213> ORGANISM: Artificial Sequence
<220> FEATURE:
<221> NAME/KEY: misc_feature
<222> LOCATION: (23)..(25)
<223> OTHER INFORMATION: N= A, C, G or T
<223> OTHER INFORMATION: Description of Artificial Sequence: primer

<400> SEQUENCE: 7
tttttttttt ttgcgatccc cannn                                             25
```